(12) United States Patent
Churchill

(10) Patent No.: US 8,057,096 B2
(45) Date of Patent: Nov. 15, 2011

(54) DENTAL RADIOGRAPH SENSOR POSITIONING DEVICE

(76) Inventor: Scott P. Churchill, Fair Oaks, CA (US)

( * ) Notice: Subject to any disclaimer, the term of this patent is extended or adjusted under 35 U.S.C. 154(b) by 0 days.

(21) Appl. No.: 12/458,295

(22) Filed: Jul. 8, 2009

(65) Prior Publication Data

US 2011/0007879 A1   Jan. 13, 2011

(51) Int. Cl.
*A61B 6/14* (2006.01)
(52) U.S. Cl. ............... 378/191; 378/169; D24/161
(58) Field of Classification Search .......... 378/168–170, 378/191; D24/154, 161
See application file for complete search history.

(56) References Cited

U.S. PATENT DOCUMENTS

| | | | | |
|---|---|---|---|---|
| 2,005,993 A * | 6/1935 | Heron et al. | | 378/170 |
| 2,522,201 A * | 9/1950 | Stern | | 378/170 |
| 4,144,460 A * | 3/1979 | Norman | | 378/170 |
| 4,251,732 A * | 2/1981 | Fried | | 378/170 |
| 4,731,808 A * | 3/1988 | Ogunsunlade | | 378/170 |
| 5,090,047 A | 2/1992 | Angotti et al. | | |
| 5,422,927 A * | 6/1995 | Schmitz | | 378/170 |
| 5,737,388 A | 4/1998 | Kossila | | |
| 6,461,038 B2 | 10/2002 | Pellegrini et al. | | |
| 7,097,356 B2 | 8/2006 | Calderwood et al. | | |
| 7,226,208 B2 | 6/2007 | Schmulenson | | |
| 7,290,928 B2 | 11/2007 | Calderwood et al. | | |
| 2008/0025468 A1 | 1/2008 | Schmulenson et al. | | |

* cited by examiner

*Primary Examiner* — Edward Glick
*Assistant Examiner* — Thomas R Artman
(74) *Attorney, Agent, or Firm* — Theodore J. Bielen, Jr.

(57) ABSTRACT

A dental radiograph sensor positioning device utilizing an elongated member which is fixed to a pair of supports. The first and second supports include holders for the radiograph sensor and are used interchangeably for this purpose. When one of the supports is held to the sensor, the other support is used as a grip for the user of the device. In this manner the device of the present invention may be used to obtain digital images from all four dental quadrants.

4 Claims, 2 Drawing Sheets

DENTAL RADIOGRAPH SENSOR POSITIONING DEVICE

BACKGROUND OF THE INVENTION

The present invention relates to a novel and useful dental radiograph sensor positioning device.

Dental radiographs provide essential information concerning the teeth of patients. Digital dental radiography is a recent development in the dental field and produces images utilizing very low levels of radiation, when compared to traditional x-rays which create dental radiographs on film. Instead of using film, the dental clinician creates dental images using a small electronic sensor or an image receptor that is placed in the mouth of the patient to capture the image. The digital radiograph image obtained in this manner is transmitted to a computer processor where the image may be viewed quickly on a computer screen. The clinician can also determine the quality of the image and either retake the image or correct the image via a computer program. Such corrections, may include the application of magnification to enhance specific problem areas shown in a tooth, and/or the altering of brightness and contrast of the image. Needless to say, digital images may be printed or copied and stored in a computer memory unit. Thus, the disadvantages of using film is a avoided by employment of digital radiograph techniques i.e. necessary film processing and time delays in viewing images. To conduct digital dental radiograph it is, necessary to position a digital sensor against the lingual side of a tooth within a mouth of a patient. In the past, holders for digital sensors or x-ray plates have been proposed. For example, U.S. Pat. No. 5,737,388 shows a holder for picture plates or x-ray film utilizing a plate which is rotatably fixed to and alignment rod in order to properly align the x-ray plate with the source of x-rays.

U.S. Pat. Nos. 5,090,047 and 6,461,038 describe image receptor mechanisms which include a shafts that terminate in slots or loops to hold the x-ray sensor in place against the patient tooth.

U.S. Pat. No. 7,226,208 and United States Patent Publication 2008/0025468 describe holders for x-ray sensing devices which include retention mechanisms located on either end of a rod. One retention member includes a slot for a sensor while the other one is employed to hold x-ray film.

U.S. Pat. Nos. 7,097,356 and 7,290,928 show radiographic sensor positioning systems which employ a handle and a ring shaped member that slides into either the posterior imaging or anterior imaging bar. The posterior imaging bar is preferably T-shaped and provides a platform for the sensor.

A dental radiographic sensor positioning device which is simple and versatile in the imaging any tooth of a patient would be a notable advance in the dental arts.

BRIEF SUMMARY OF THE INVENTION

In accordance with the present application a novel and useful dental radiograph sensor positioning device is herein provided.

The device of the present application utilizes an elongated member. A first support having a first connector fastens to the elongated member. The first support includes a first surface and an opposite second surface with an end portion therebetween. The first support is provisioned with a holder for maintaining the radiograph sensor adjacent the first surface of the first support.

A second support is also included in the present invention and possesses a first surface with an opposite second surface. An end portion lies between the first and second surfaces of the second support. The second support further comprises a holder which is also capable of maintaining the radiographic sensor adjacent the first surface of the first support. The second support includes a second connector which fastens the second support to the elongated member at a position spaced from the first support. The first and second supports lie along the elongated member with the end surfaces of the first and second supports being adjacent from one another. The first surfaces of the first and second supports are similarly oriented relative to the elongated member. Thus, the user of the device of the present invention may use either the first or second support to hold the radiographic sensor, while using the remaining support as a grip for manipulating the same during the process of obtaining radiographic images.

The device of the present invention is also formed with a guide which is slidingly mounted to the elongated member between the connected first and second supports. The guide may be employed to mount a wire connected to the radiographic sensor so as not to allow the wire to interfere with the obtaining of radiographic images.

It may be apparent that a novel and useful radiographic sensor positioning device has been hereinabove described.

It is therefore an object of the present invention to provide a dental radiographic sensor positioning device that easily and efficiently mounts a radiographic sensor which is capable of obtaining radiographic images of any teeth found in the mouth of a patient.

Another object of the present invention is to provide a dental radiographic sensor positioning device which allows the mounting of a radiographic sensor in any one of a pair of supports in order to quickly and easily manipulate the device in the mouth of a dental patient to obtain radiographic images.

Another object of the present invention is to provide a dental radiographic sensor positioning device in which a support for the radiograph sensor may also be used as a grip by the user of the device.

Yet another object of the present invention is to provide a dental radiographic sensor positioning device which eliminates the need to employ radiograph sensors that are of a left-handed and right-handed configuration.

Another object of the present invention is to provide a dental radiographic sensor positioning device which is economical to produce and is easily sterilized.

The invention possesses other objects and advantages especially as concerns particular characteristics and features thereof which will become apparent as the specification continues.

Figure 1:
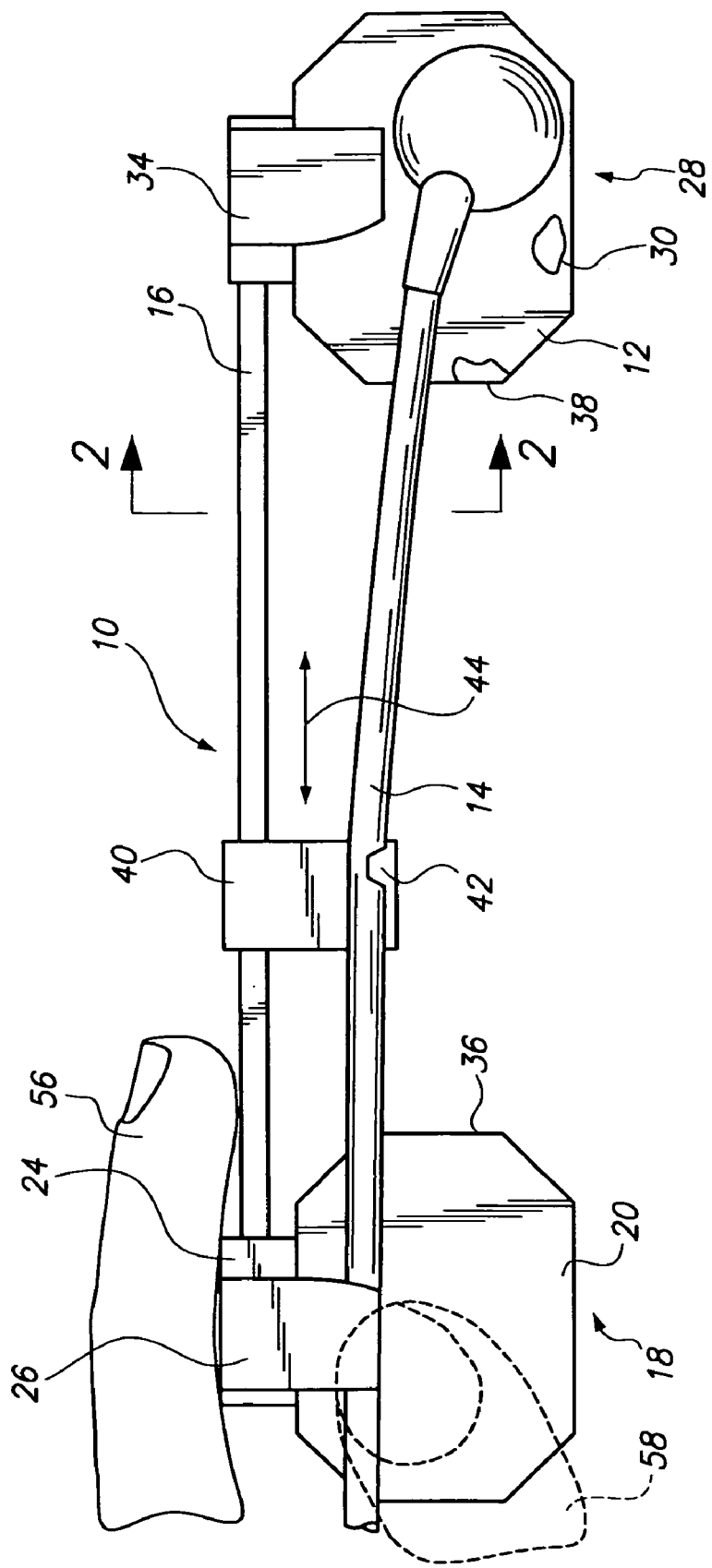
FIG. 1 is a front elevational view of the dental radiographic sensor positioning device of the present invention, showing the fingers of the users in phantom or in partial rendition.

For a better understanding of the invention reference is made to the following detailed description of the preferred embodiments of the invention which should be taken in conjunction with the above described drawings.

DETAILED DESCRIPTION OF THE PREFERRED EMBODIMENTS OF THE INVENTION

Various aspects of the present invention will evolve from the following detailed description of the preferred embodiments thereof which should be referenced to the prior described drawings.

An embodiment of the invention as a whole is shown in the drawings by reference character 10. Device 10 is intended to be used with a radiograph sensor 12 having a wire or cable 14 which is intended to transmit data from sensor 12. Sensor 12 is capable of creating digital signals which pass through cable 14 and lead to a computer or other digital device (not shown) for the viewing and recording of such images.

Device 10 includes in one of its elements and elongated member 16, which may be formed as a rigid or semi-rigid metallic rod. Elongated member 16 is of sufficient length to manipulate device 10 within a mouth of a dental patient, FIG. 1.

A first support 18 is utilized in the device 10 of the present invention. First support 18 possesses a first surface 20 and an opposite second surface 22. A connector 24 fastens first support 18 to elongated member 16 by any suitable means such as gluing, sonic welding, unitary construction, and the like. Connector 24 and first support 18 may be formed of any suitable material which is easily sterilized, such as polymeric material. In addition, first support 18 possesses a holder 26 which may be employed to maintain the radiographic sensor 12 adjacent first surface 20 of first support 18. Holder 26 may take the form of a clip which is formed of resilient material such that sensor 12 is held to surface 20 of first support 18 by a spring action.

Figure 2:
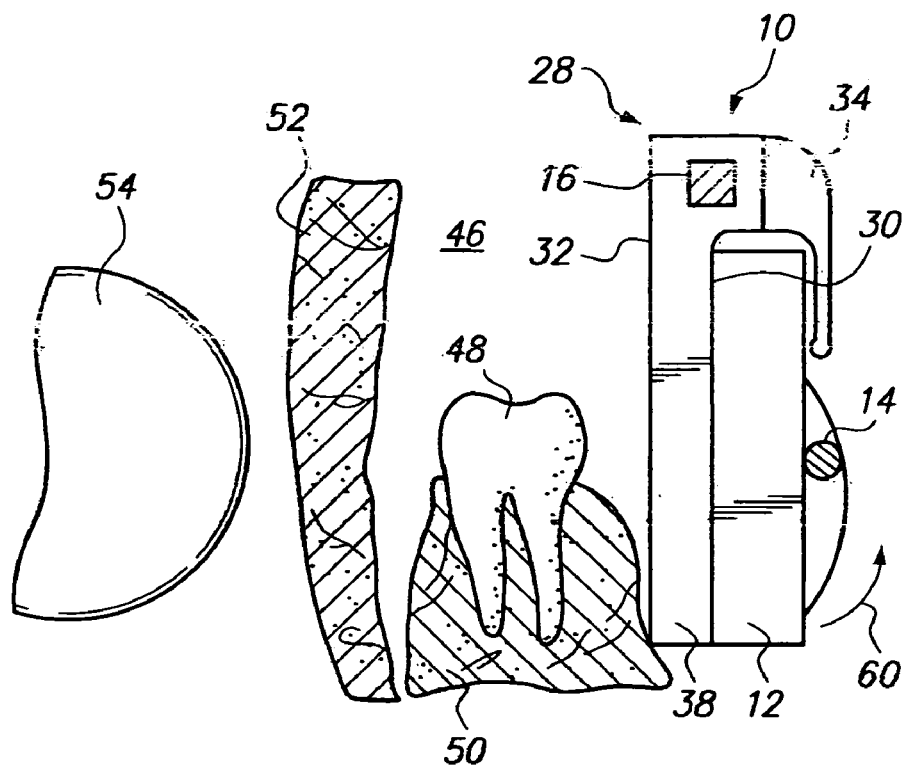
FIG. 2 is a sectional view taken along line 2-2 of FIG. 1 with the addition of a tooth, and the gum and cheek anatomy shown in section, for the lower left quadrant of a patient mouth.

Likewise, a second support 28, shown in FIG. 2, is also provided and includes a first surface 30 and a second surface 32. Holder 34 of second support 28 is capable of maintaining sensor 12 adjacent first surface 30 of second support 28 and is similarly constructed to holder 26, associated with first support 18. Sensor 12 is depicted in FIGS. 1 and 2 as being maintained against holder 28, in this regard. Edges 36 and 38 of first and second holders 18 and 28 respectively, lie adjacent to one another, where first and second supports 18 and 28 are spaced from one another along elongated member 16. In addition, first surfaces 20 and 30 of first and second supports 18 and 28, respectively, are similarly oriented relative to the elongated member 16. That is to say, surfaces 20 and 30 generally face in the same direction as one another.

Guide 40 is also employed in device 10 to manage wire or cable 14 which feeds to sensor 12. Guide 40 possesses a spring loaded appendage 42 which allows the user to snap wire 14 into place on guide 40, as shown in FIG. 1. Guide 40 is slidable relative to elongated member 16 in order to position wire 14 in a convenient place at the predilection of the user of device 10, directional arrow 44.

In operation, device 10 is employed to obtain radiographic images by the use of sensor 12. As depicted in FIGS. 1 and 2, sensor 12 is mounted to second support 28 and is placed in the mouth cavity 46 of the patient adjacent tooth 48, projecting from gum 50. Cheek 52 separates tooth 48 from x-ray source 54. X-ray emanating from source 54 pass through tooth 48 and a digital image is obtained by sensor 12. Such image is transmitted through cable or wire 14 to an appropriate viewing and recording apparatus. As shown in FIG. 1, second support 28 holding sensor 12 spaces from support 18, which is itself grasped by the index finger 56 and the thumb 58 of the user of the device 10. Thus, support 18 is being employed as a grip. It should also be noted, that wire 14 may be garnered by holder 26 of first support 18. With reference to FIG. 2, it may be seen that the device 10 in the orientation of FIG. 1 is used to obtain an image from tooth 48 in the lower left quadrant of the mouth cavity 46 of a patient. Device 10 is then flipped 180 degrees, according to directional arrow 60, and images are taken of the upper right quadrant of mouth cavity 46 of the patient. Thus, elongated member 16 does not interfere with certain structures of the patients mouth such as the teeth, roof of the mouth, and the like in this regard.

Figure 3:
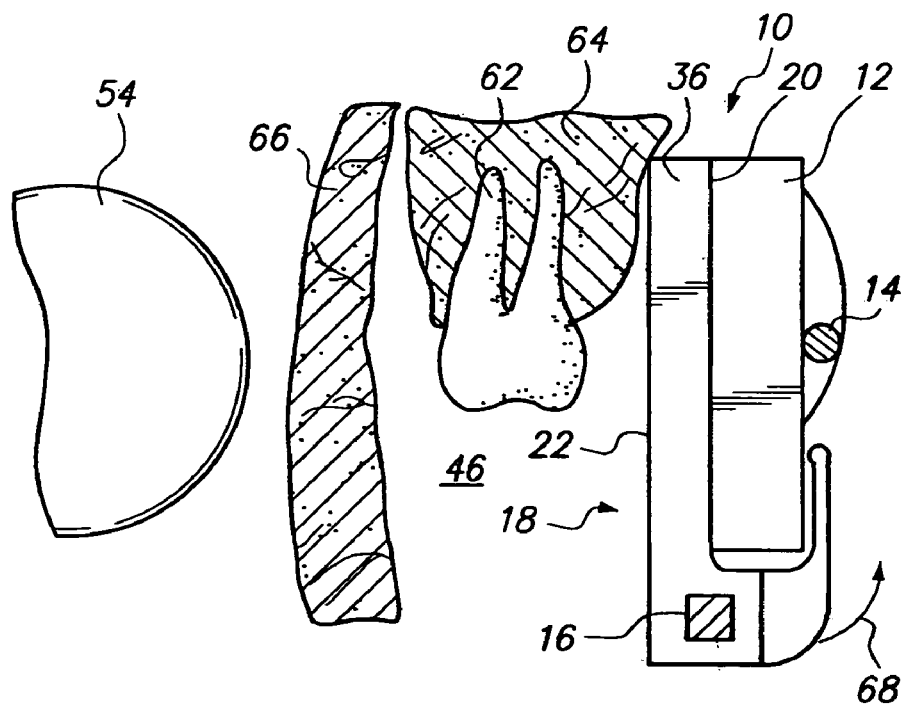
FIG. 3 is a view similar to that shown in FIG. 2 with the device of the present invention being used to obtain an image from the upper left quadrant of the mouth of a patient by repositioning the radiograph sensor to another support on the device of the present invention.

To obtain images from the upper left quadrant and the lower right quadrant of the patient, sensor 12 is moved from second support 28 to first support 18 and wire 14 is held by guide 40 and, optionally, by holder 34 of second support 28. The dental practitioner then employs second support 28 as a grip to obtain images from upper left quadrant and lower right quadrant of the patient mouth cavity 46. FIG. 3 depicts the position of device 10 in the upper left quadrant of patient mouth 46 with respect to tooth 62 extending from gum 64. Again, cheek 66 intercedes source 54 and tooth 62. Following the obtaining of digital images from tooth 62, device 10 is then rotated 180 degrees, directional arrows 68 of FIG. 3, to obtain digital images from the lower right quadrant of the mouth cavity of the patient. Again, elongated member 16 does not pose any interference with the anatomical regions of the person mouth by this process. In the embodiment depicted in FIG. 3, second support 28 is used as a grip.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. a device for positioned radiograph sensor within the mouth of a patient comprising:
   a. an elongated member,
   b. a first support, said first support including a first surface and an opposite second surface with an end surface therebetween, said first support further comprising a clip for maintaining the radiograph sensor adjacent said first surface of said first support and positioned along the length of and apart from said elongated member;
   c. a first connector for fastening said first support to said elongated member;
   d. a second support said second support including a first surface and an opposite second surface, with an end surface therebetween, said second support further comprising a clip for maintaining the radiographic sensor adjacent said first surface of said second support, and positioned along the length of and apart from said elongated member;
   e. a second connector for fastening said second support to said elongated member, said second support being spaced from said first support, said first support and said second support each lying along and each distending in the same direction from said elongated member with said end surfaces of said first and second supports being adjacent and spaced from each other, said first surfaces of said first and second supports being similarly oriented relative to said elongated member.

2. The device of claim 1 in which said first and second holders are formed of resilient material.

3. The device of claim 1 in which the radiograph sensor includes a wire and said device further comprises a guide for said wire.

4. The device of claim 3 in which said guide is slidably mounted to said elongated member between said first and second supports.

* * * * *